United States Patent [19]

Klemarczyk et al.

[11] Patent Number: 5,070,117
[45] Date of Patent: Dec. 3, 1991

[54] AROMATIC VINYL ETHER COMPOUNDS AND COMPOSITIONS, AND METHOD OF MAKING THE SAME

[75] Inventors: Philip T. Klemarczyk, Collinsville; Yoshihisa Okamoto, Avon, both of Conn.

[73] Assignee: Loctite Corporation, Hartford, Conn.

[21] Appl. No.: 615,205

[22] Filed: Nov. 19, 1990

Related U.S. Application Data

[62] Division of Ser. No. 543,248, Jun. 25, 1990, Pat. No. 5,004,842.

[51] Int. Cl.$^5$ .......................... C08F 2/46; C08F 12/24; C08T 3/28; C07C 41/00
[52] U.S. Cl. ...................................... 522/31; 522/181; 568/640; 568/641; 526/313
[58] Field of Search ................... 522/31, 181; 568/640, 568/641; 526/313

[56] References Cited

U.S. PATENT DOCUMENTS 5,004,842  4/1991  Klemarczyk et al. ............... 568/640

Primary Examiner—Marion E. McCamish
Assistant Examiner—Mark A. Chapman
Attorney, Agent, or Firm—Steven J. Hultquist

[57] ABSTRACT

An aromatic vinyl ether of the formula:

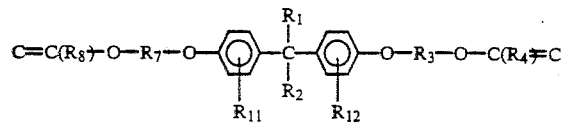

wherein:
$R_1$, $R_2$, $R_4$, $R_5$, $R_6$, $R_8$, $R_9$, and $R_{10}$ are independently selected from hydrogen, halogen, and $C_1$-$C_8$ alkyl radicals;
$R_3$ and $R_7$ are independently selected from $C_1$-$C_6$ alkylene radicals; and
$R_{11}$ and $R_{12}$ are independently selected from allyl and methallyl.

Also disclosed are various other aromatic vinyl ether compounds, chain-extended derivatives thereof, and liquid vinyl ether blends, and a method of making the aromatic vinyl ether compounds at high yield. The aromatic vinyl ether compounds, chain-extended vinyl derivatives, and/or liquid vinyl ether blends of the invention may be employed as vinyl ether components together with cationic photoinitiators, to provide cationically polymerizable vinyl ether compositions having utility in applications such as coatings, adhesives, and sealants.

7 Claims, No Drawings

AROMATIC VINYL ETHER COMPOUNDS AND COMPOSITIONS, AND METHOD OF MAKING THE SAME

REFERENCE TO RELATED APPLICATION

This is a division of U.S. application Ser. No. 07/543,248 filed June 25, 1990, now U.S. Pat. No. 5,004,842.

BACKGROUND OF THE INVENTION

1. Field of The Invention

This invention relates to aromatic vinyl ether compounds and compositions which are cationically polymerizable in the presence of a suitable photoinitiator under photopolymerization conditions, and also relates to a method of making such aromatic vinyl ether compounds and compositions.

2. Description of The Related Art

In the field of radiation-cured materials, for applications such as adhesives, sealants, and coatings, significant effort has been directed to developing cationically polymerizable, radiation-curable materials. Such interest in cationically curable materials is a consequence of the potential advantages of such compositions over conventional free radical-initiated radiation-curable materials, such as (meth)acrylates.

Currently, there are three primary categories of radiation curable systems-(meth)acrylates, thiol-enes, and epoxies. The most popular of these systems is the (meth)acrylate-based UV free radical curing system, for which a wide variety of suitable prepolymers is commercially available. These (meth)acrylate-based UV curing systems, however, suffer from deficiencies associated with the odor and toxicity of acrylate monomers, poor adhesion, and oxygen inhibition effects.

Thiol-ene UV free-radical curing systems have been developed, such as the thio/norbornene systems reported in Jacobine, A., *Polymeric Materials Sci. Eng.*, 60, 211. 1989. These systems yield flexible coatings, but have the disadvantages of thiol odor and poor adhesion characteristics.

Epoxy-based UV cationically curable systems are known. Since the development of UV cationic initiators in the 1970's (see Crivello, J. V., et al, *Macromolecules*, 10, 1307 (1977)), UV cationically curable systems have attracted increasing interest and have gained in popularity as a radiation cure technology.

Relative to free-radical initiated, radiation-curing systems, UV cationic cure systems have the advantages of higher curing speeds, lack of oxygen inhibition, dark curing (i.e., continuation of cure even after cessation of UV radiation exposure), superior shelf-stability, lower toxicity, and lower odor characteristics.

Despite their many advantages, however, UV cationic cure systems technology has been hindered by limited availability of commercially useful monomers, and associated high costs of those monomers which are commercially available.

The development of epoxy-based UV cationically curing compositions has met with limited success. One of the most versatile and widely employed epoxy resins is diglycidyl ether of Bisphenol A (DGEBPA). Despite its widespread and successful use in non-cationic curing systems, DGEBPA and numerous other epoxy resins are characterized by unsuitably low curing rates in UV cationic curing systems. At present, the only widely available epoxy materials which are suitable for use in rapid UV cationically curing systems, are alicyclic diepoxides (see Koleske, J. V., *RadTech '88-North American Conference Papers*, 353 (1988)), such as

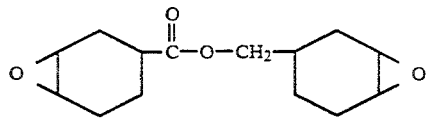

which is commerically available under the trademark Cyracure UVR 6100 (Union Carbide Corporation; Danbury, Conn.).

It is known that vinyl ether monomers are readily polymerizable by cationic polymerization, and a variety of vinyl ether monomers have been synthesized, however, prior to the 1970's, cationic polymerization vinyl ether technology was not practical due to severe polymerization conditions, e.g., polymerization reaction temperatures on the order of $-70°$ C., which were required to cationically polymerize vinyl ether monomers. Beginning in the mid-1970's, UV photocationic initiators were developed, which initiate the polymerization of vinyl ether monomers at room temperature conditions.

As a result of the development of UV cationic initiators, UV cationically curable vinyl ether and epoxy systems have attracted interest, and some vinyl ether and epoxy cationically curable systems are now commercially available. As indicated, however, the number of such monomers is limited and the costs of such monomers are significant in comparison to monomers employed in free-radical initiated polymerization systems.

Commercially available vinyl ether monomers which are curable by UV cationic cure methods (see Dougherty, J. A., et al, *RadTech '88-North American Conference Papers*, 372 (1988)) include vinyl ether monomers of the formulae:

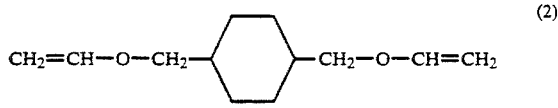

These vinyl ether monomers are cationically curable at much faster rates than the commercially available cationically curable epoxy systems. Since these vinyl ether compounds have aliphatic (Formula 1) and cycloaliphatic (Formula 2) backbone structures, respectively, their glass transition temperatures ($T_g$'s) are so low (20° C. and 80° C., respectively) that they are practically useful only as reactive diluents for UV cationic curing epoxy systems.

In order to overcome the problems associated with such low $T_g$ values of the above-described vinyl ether monomers, divinyl ether monomers possessing an aromatic backbone structure have been developed, e.g., the bisphenol backbone monomer of the formula:

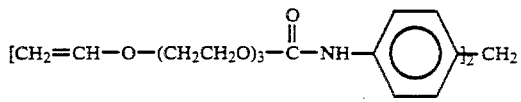

The problem with such type of vinyl ether compounds is that the urethane linkages

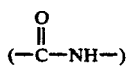

significantly slow the UV cationic curing rate of the monomer. Although the urethane moiety is not as strong a base as an amine or other active hydrogen species, the urethane group acts as a weak counter anion in cationic polymerization systems, thereby retarding the rate of cationic polymerization of the vinyl ether monomers. In other, less reactive UV cationically curable monomers systems, such as those comprising alicyclic epoxies, the presence of urethane groups completely inhibits the UV cationic cure.

In an effort to overcome the slow or non-curing characteristics of urethane-containing vinyl ether monomers, vinyl ether compounds have been developed which contain only ether linkages, such as the Bisphenol A-based vinyl ether compound of the formula:

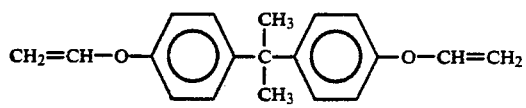

The problem with vinyl ether compounds of such type is that the aromatic vinyl ether rearranges to yield only low molecular weight polymers containing pendant phenolic groups, as shown in the following model reaction (see Crivello, J. V., *J. Polymer Sci., Polymer Chem. Ed.*, 21, 1785 (1983)):

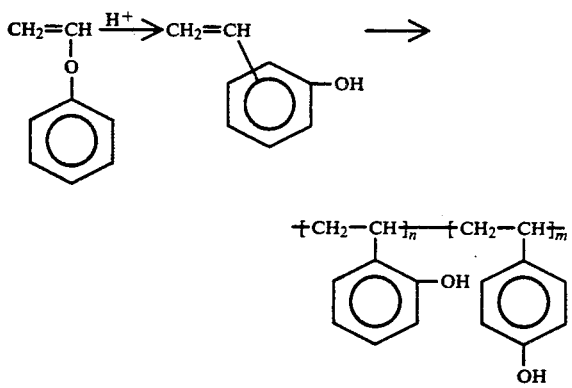

Such rearrangement problem was overcome by incorporation of an alkylene (ethylene) group between the phenoxy and vinyloxy moieties of the aromatic vinyl ether molecule in Bisphenol A-based compounds such as:

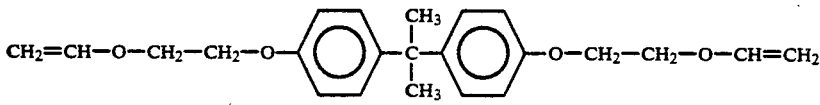

This compound contains a rigid aromatic (Bisphenol A residue) backbone which is similar in structure to the backbone of DGEBPA epoxy resins. As a result, the cured properties of such vinyl ether compound, such as flexural modulus, heat distortion temperature, and glass transition temperature, are close to the cured properties of DGEBPA. In addition, this aromatic vinyl ether compound cures significantly faster than the corresponding epoxy system, e.g., a composition comprising an alicyclic epoxy such as 4-vinylcyclohexene dioxide, and DGEBPA. The Bisphenol A-based divinyl ether compound is an excellent resin, but unfortunately suffers a major deficiency in that it is a solid at room temperature (with a melting point on the order of 55°-57° C.), and thus cannot be satisfactorily used in adhesive and coating applications.

Thus, aromatic backbones such as Bisphenol A-based structures are essential to provide adequate rigidity and toughness in the cured vinyl ether resin. The majority of divinyl either compounds containing an aromatic backbone structure, however, are solids at room temperature and have melting points substantially above 25° C. (See Crivello, J. V., *J. Polymer Sci., Polymer Chem. Ed.*, 21 1785 (1983).

In an effort to obtain liquid divinyl ether monomers containing an aromatic backbone structure, chain-extended compounds have been synthesized as reaction products of aromatic divinyl ether monomers with active hydrogen compounds such as aryl polyols, e.g., Bisphenol A, to yield liquid reaction products. These chain-extended compounds cure to form products which are less brittle than the polymerized divinyl ethers obtained from non-chain-extended monomers, due to the lower cross-linking density achievable with the chain-extended compounds. Unfortunately, the chain-extended compounds are characterized by high viscosity and by the presence of acetal linkages which are hydrolytically unstable, resulting in the undesired formation of formaldehyde, phenol, and hydroxy-functional reaction products.

U.S. Pat. No. 3,803,246 issued Apr. 9, 1974 to K. S. Rosenzweig, et al discloses the formation of oxyalkylated diphenol compositions by reacting diphenol with an alkylene oxide in the presence of lithium hydroxide or lithium acetate. The patent notes at column 1, lines 48–55 that when the corresponding diphenol/alkylene oxide reaction is carried out in the presence of sodium hydroxide, the product contains, in addition to alkoxylated diphenols, substantial amounts of oxyalkylated decomposition products of diphenol, such as oxylalkylated phenol and oxyalkylated isopropenyl phenol. These diphenol decomposition products are said to be substantially reduced by the use of the lithium hydroxide or lithium acetate constituent. The patent at column 2, lines 50–52 also discusses reacting the product oxyalkylated diphenol with additional alkylene oxide in the presence of a "non-lithium containing alkoxylation catalyst." The patent lists various diphenols which may be employed to form the oxyalkylated diphenol product, including bisphenol compounds wherein the aromatic moiety comprises a methyl substituent on the ring. The patent discloses to form polyesters of allegedly improved properties, by esterifying the oxyalkylated diphenol compounds with dicarboxylic acids or anhydrides. The patent discloses that at least 80 mole percent of the dicarboxylic acid or anhydride preferably is ethylenically unsaturated dicarboxylic acid or anhydride. Example VII of the patent discloses the reaction of 2,2-bis(4-hydroxy-3-methyl-phenyl) propane with ethylene oxide in the presence of lithium hydroxide monohydrate, with a resulting product then being reacted with ethylene oxide in the presence of sodium hydroxide to yield polyoxyethylene (14) 2,2-bis(4-hydroxy-3-methyl-phenyl) propane. The patent at column 2, lines 20-30 discloses the diphenol reactant as being substitutable on the phenylene rings with $C_1-C_4$ alkyl.

U.S. Pat. No. 4,603,162 issued July 29, 1986 to Y. Hasegawa, et al describes a radiation curable resin of the formula:

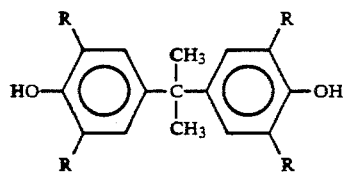

wherein R is a methylol group or (meth)acrylated methylol group. The molar ratio of methylol to (meth)acrylated methylol substituents is preferably in the range of 20:1 to 1:3. The resin is formed by reacting Bisphenol A with formaldehyde in the molar ratio of 1:4, to yield tetramethylol Bisphenol A, and reacting the methylolated product with acrylic acid, methyacrylic acid, or a lower alcohol ester thereof, yielding the (meth)acrylated product.

U.S. Pat. No. 4,622,376 issued Nov. 11, 1986 to M. S. Misura, et al discloses a pourable polymerizable composition comprising (1) an aromatic-containing poly(allyl carbonate)-functional material comprising aromatic-containing bis(allyl carbonate)-functional monomer and/or aromatic-containing poly(allyl carbonate)-functional polymer, (2) styrenic material, and (3) polyethylenic-functional monomer containing three or more allyl, methallyl, acrylyl and/or methacrylyl groups. The patent discloses in the paragraph bridging columns 2 and 3 of the patent that the aromatic-containing bis(allyl carbonate)-functional monomers comprise a divalent radical derived from a dihydroxy aromatic-containing material, which may be a polyol-functional chain-extended compound. The reference discloses that the aromatic rings in such bisphenol may include substituents such as $C_1-C_4$ alkyl, phenyl, or halo. At column 7, lines 3-27, the patent discloses that a wide variety of compounds may be used as the polyethylenic functional monomer containing three or more allyl, methyallyl, acrylyl, and/or methacrylyl groups.

U.S. Pat. No. 4,439,291 issued Mar. 27, 1984 to E. Irving, et al describes a polymerizable composition including (1) a compound containing (a) at least one acryloyloxy and/or methacryloyloxy group, and (b) at least one allyl, methallyl, and/or 1-propenyl group attached directly to a carbon atom which forms part of an aromatic nucleus or to an oxygen atom or oxycarbonyl group which in turn is directly attached to such a carbon atom, in which the total number of groups (a) and (b) is at least three, and (2) a compound containing at least two mercaptan groups directly attached to aliphatic carbon atoms, in in a specified proportion of mercaptan groups to the other specified functional groups. Among the compounds (1) disclosed in the patent specification are: 2,2-bis(3-allyl-4-(methacryloyloxy)phenyl) propane [column 5, line 49]; and the corresponding methallyl compound [column 5, line 51]. The polymerizable composition disclosed in this reference may contain a photosensitizing agent and a heat-activated free-radical catalyst for two-stage curing, comprising initial exposure to actinic radiation followed by heating, to form cured compositions useful in applications such as coatings, adhesives, and reinforced composites. In its "Background" section, this patent identifies U.S. Pat. No. 4,220,513 as disclosing 2,2-bis(3-allyl-4-(glycidyloxy)phenyl) propane, and U.S. Pat. No. 4,308,367 is identified as disclosing 2,2-bis(3-allyl-4-hydroxyphenyl)propane. Various 2,2-bis(allyl-((meth)acryloxyalkoxy)-phenyl)propane compounds are described in the patent; see, for example formula XXXIV at column 20 of the specification, and formula XXXVIII at column 22 thereof.

U.S. Pat. No. 4,683,327 issued July 28, 1987 to R. W. Stackman describes heat-curable acrylic-terminated aromatic monomers wherein the monomer backbone comprises oxycarbonyl groups alternating with divalent aromatic radicals, and wherein the backbone may comprise $C_1-C_4$ alkoxy groups. The patent specification in the sentence bridging columns 4 and 5 discloses that the hydrogen atoms present on the aromatic rings may be replaced by alkyl, alkoxy, halogen, phenyl, and substituted phenyl substituents.

U.S. Pat. No. 4,388,450 issued June 14, 1983 to J. V. Crivello describes cationically curable compositions comprising aromatic polyvinylethers, such as 2,2-bis(p-vinyloxy-ethoxyphenyl) propane, and "reaction products of such materials with various active hydrogen compounds, for example, polycarboxylic acids, phenols, silanes, thiols, etc." (column 2, lines 5-8). The thermal curing catalyst employed with such compositions comprises an aryl/onium salt, and an organic oxidant or an aromatic polyvinylether-soluble copper compound. A wide variety of vinyloxyalkoxy aromatic compounds are disclosed. The patent as indicated teaches to further react the aromatic polyvinylether compound with a phenolic reactant such as Bisphenol A (column 6, lines 30-35). The patent discloses to make the aromatic vinyl ether compounds by condensing an alkali metal-aryl hydroxide or acid salt with a haloalkyl-vinylether in the presence of dimethylsulfoxide.

At column 8, lines 26-30, the patent discloses that the curable composition may be formed by melt-blending:

"Depending on upon the particular ingredients used in the heat curable mixture, melt blending can be used in certain instances, particularly where the aromatic polyvinylether has a melting point of 25° C. to 100° C. Otherwise, solvent blending can be used."

U.S. Pat. No. 4,864,054 issued Sept. 5, 1989 to J. V. Crivello, et al describes 1-propenyl aromatic vinyl ethers, including various Bisphenol A-based compounds. The patent teaches in Example I (column 8, lines 45 et seq.) to form a bisallylether of Bisphenol-A by reacting bisethoxylated Bisphenol-A with allylchloride in the presence of sodium hydroxide and tetrabutylammonium bromide.

U.S. Pat. No. 4,518,788 issued May 21, 1985 to J. V. Crivello discloses aromatic polyvinylethers comprising vinyloxyalkoxy substituents on an aromatic moiety, and reaction products of same with active hydrogen compounds such as polycarboxylic acids, phenols, thiols, silanes, and polyols. Compositions comprising such vinyl ether compounds are rendered heat-curable by a thermal curing catalyst comprising an onium salt in combination with an organic oxidant or an aromatic polyvinylether-soluble copper compound.

U.S. Pat. No. 4,705,887 issued Nov. 10, 1987 to J. V. Crivello stands in divisional relationship to U.S. Pat. No. 4,518,788, discussed above. The '887 patent claims the reaction products of the aromatic polvinylether compounds (claimed in the '788 patent per se) with active hydrogen compounds of various specified types.

U.S. Pat. No. 4,617,238 issued Oct. 14, 1986 to J. V. Crivello, et al describes the formation of photo-curable vinyloxy-functional polysiloxanes by hydrosilation of compounds containing both allyl and vinyl ether functional groups. In the paragraph bridging columns 4 and 5 of the patent, it is taught to form the allyl vinyl ether reactant by adding vinyloxy functionality to an ally-functional compound. Preferred allyl-functional compounds are allyl phenols, with eugenol being most preferred. Column 5, lines 25-39 discloses the reaction of eugenol with 2-chloroethyl vinyl ether, to form an allyl vinyl ether compound wherein the benzene ring is substituted by allyl, methoxy, and vinyloxyethoxy substituents. Such allyl vinyl ether then is reacted with the silane to form the product vinyloxy-functional polysiloxane product. This reaction is said to be based on the discovery that the rate of silane addition to allyl vinyl ethers is much faster at the allyl site than at the vinyl site (column 3, lines 58-61). See Examples 5-6 of the patent, relating to the synthesis of allyl-and vinyloxyethoxy-substituted benzene compounds.

U.S. Pat. No. 4,442,197 issued Apr. 10, 1984 to J. V. Crivello, et al describes UV photocurable, cationically polymerizable compositions including a cationically polymerizable organic material and a photoinitiator selected from a dialkylphenacyl sulfonium salt of specified formula, sensitized with an effective amount of a polynuclear aromatic hydrocarbon and/or phenothiazine, or a hydroxyaryldialkyl sulfonium salt of specified formula, sensitized with an effective amount of an aromatic ketone. Among the cationically polymerizable organic materials which are disclosed to be useful in the curable compositions described in this patent are vinyl organic prepolymers including multifunctional vinyl ethers (see, generally, column 4, line 55 to column 7, line 40). Among the polyvinyl compounds disclosed (at column 6) in the patent are Bisphenol A divinyl ethers.

U.S. Pat. No. 3,933,509 issued Jan. 20, 1976 to Y. Noguchi, et al describes a photopolymerizable composition comprising a cationically polymerizable substance and a photopolymerization initiator comprising at least one inorganic or organic acid salt of an indolinobenzospiropyran of specified formula. As the cationically polymerizable substance, the patent describes vinyl ethers and N-vinyl compounds as preferred materials. The patent also discloses poly-functional vinyl ethers as being useful alone or in combination with a mono-functional monomer, citing 2,2-bis-(3',5'-dibromo-4'-vinyloxyethoxyphenyl) propane and 2,2-bis-(p-vinyloxy-ethoxyphenyl) propane as poly-functional species (column 6, lines 48-60). At column 6, lines 67-68, the patent discloses that "[t]he cation polymerizable compounds can be used alone or in a combination of two or more."

U.S. Pat. No. 4,749,807 issued June 7, 1988 to S. C. Lapin, et al describes vinyl ether-terminated ester oligomers which are cationically polymerizable by radiation in the presence of an onium salt. The vinyl ether compounds disclosed in this patent have one or more terminal vinyl ether groups and are oligomeric esters of carboxylic acids which contain oxycarbonyl linkages in the backbone structure. At column 4, lines 18-22, the patent teaches the reaction of a vinyl ether terminated alcohol, a second polyol, and carboxylic acid, wherein the polyol acts as a chain extender by ester formation with the carboxylic acid.

The vinyl ether polyester compounds disclosed in Examples I and III of the patent are aromatic liquids.

U.S. Pat. No. 4,751,273 issued June 15, 1988 to S. C. Lapin, et al discloses to form vinyl ether terminated urethane resins, which are produced by reacting acetylene and a glycol with a diisocyanate. The patent discloses at column 6, lines 24-28 that the resins of the patent may be cured by UV radiation in the presence of an aryl-onium salt.

U.S. Pat. No. 4,230,814 issued Oct. 28, 1980 to J. V. Crivello describes heat curable compositions comprising a cationically polymerizable organic material which is thermally cured with an organic oxidant such as an organic peroxide, in combination with an effective amount of hydroxyaryldialkyl sulfonium salts of specified formula. At column 4, lines 16-20, various classes of cationically polymerizable organic materials which can be used in the composition of the patent are disclosed, including vinyl organic prepolymers, such as the vinyl ether compounds described in the paragraph bridging columns 5 and 6 of the patent.

Gallucci, R. R., et al, "Synthesis of Bis(aryloxyethyl) Vinyl ethers via Phase-Transfer-Catalyzed Nucleophilic Displacement on 2-Chloroethyl Vinyl ether," *J. Org. Chem.*, Vol. 48, No. 3, 1983, 342-346, describes the preparation of bis(aryloxyethyl) vinyl ethers, using sodium hydroxide, bis(phenols), and 2-chloroethyl vinyl ether, with a tetraalkylammonium salt phase-transfer catalyst. Reaction in dimethyl sulfoxide solution is described, as well as reaction in toluene, and n-butyl alcohol. In the initial work described in this article, neat chloroethyl vinyl ether was employed as solvent (page 345). The article reports that attempts to use potassium hydroxide, lithium hydroxide, or sodium carbonate to prepare product were unsuccessful, and that potassium hydroxide gave some desired Bisphenol-A divinyl ether product but appeared to react preferentially with the chloroethyl vinyl ether component.

Neckers, D. C., "An Introduction to Stereolithography," *The Spectrum*, Vol. 2, Issue 4, Winter 1989, pages 1 and 6-10, describes stereolithography as a process for forming three-dimensional parts via photopolymerization from a photosensitive monomer such as an acrylate. On page 9, the article identifies a number of shortcomings of acrylates and posits that entirely new polymeric systems and initiation systems are in order. There follows a discussion of the work carried out by J. V. Crivello in developing photosensitive salts which were used as cationic onium photoinitiators, including aryl iodonium salts capable of producing protic acids when irradiated, for polymerizing "a living polymer from an ether or epoxide."

Accordingly, it is an object of the present invention to provide novel aromatic divinyl ether compounds and compositions, which are readily synthesized, have melting points below 25° C., and are amenable to usage in applications such as coatings, adhesives, and sealants, wherein flowable materials are desired.

Other objects and advantages will be more fully apparent from the ensuring disclosure and appended claims.

SUMMARY OF THE INVENTION

In one aspect, the present invention relates to an aromatic vinyl ether compound of the formula:

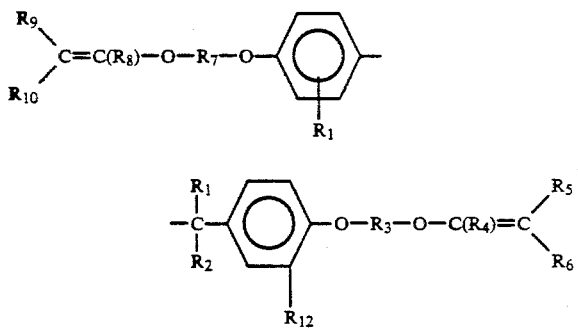

wherein:

$R_1$, $R_2$, $R_4$, $R_5$, $R_6$, $R_8$, $R_9$ and $R_{10}$ are independently selected from hydrogen, halogen, and $C_1$-$C_8$ alkyl radicals;

$R_3$ and $R_7$ are independently selected from $C_1$-$C_8$ alkylene radicals; and $R_{11}$ and $R_{12}$ are independently selected from allyl and methallyl.

In a related aspect, the present invention relates to vinyl ether blends comprising a first vinyl ether compound, of a type as described in the preceding paragraph, in combination with a second vinyl ether compound which by itself is a solid at 25° C., and which is soluble in the first vinyl ether compound, with the relative proportions of the first and second vinyl ether compounds to one another being such that the blend is liquid at 25° C.

In another aspect, the invention relates to liquid vinyl ether blends comprising at least two vinyl ether compounds, at least one of which has a melting point above 25° C., and wherein the relative proportions of the vinyl ether compounds in the blend are such that the blend is a liquid at 25° C.

In a further aspect, the invention relates to chain-extended vinyl ether compounds formed by reaction of vinyl ether compounds of the type described above, with active hydrogen compounds such as aryl polyols.

A still further aspect of the invention relates to cationically curable vinyl ether compositions including (1) a vinyl ether aromatic component comprising vinyl ether compounds of the type described above, and/or chain-extended derivatives thereof, and (2) an effective amount of a cationic photoinitiator which is initiatingly effective for polymerization of the vinyl ether component in the presence of initiating radiation.

The invention also relates to cationically curable vinyl ether compositions comprising liquid vinyl ether blends of the type described hereinabove, in combination with an effective amount of an initiatingly effective cationic photoinitiator.

A method aspect of the invention relates to a process for making an aromatic divinyl ether, comprising reacting a haloaliphatic vinyl ether compound with a polyhydroxy aromatic compound in the presence of base, a tetralkylammonium halide phase transfer catalyst, and a solvent comprising an aliphatic $C_7$-$C_{18}$ hydrocarbon solvent, to yield the aromatic divinyl ether as a reaction product.

Other aspects and features of the invention will be more fully apparent from the ensuing disclosure and appended claims.

DETAILED DESCRIPTION OF THE INVENTION, AND PREFERRED EMBODIMENTS THEREOF

The present invention relates to liquid aromatic backbone vinyl ethers which are cationically curable by exposure to UV radiation in the presence of a suitable cationic initiator.

As used herein, the term "UV radiation" refers to electromagnetic radiation having a wavelength in the range of from about 250 microns to about 700 microns.

The cationic initiator may be any suitable species affording a proton, metallic cation, or other cationic species which is curingly effective for the vinyl ether compounds and/or vinyl ether compositions of the invention, in the presence of UV radiation. Such cationic initiators include Lewis acids and proton acids. Suitable Lewis acids may include those of the Friedel-Crafts type, as well as halides of Group IIA, IIB, IIIA, IIIB, IVA, IVB, VB, and VIII elements. Such halide compounds may be employed in combination with co-catalysts such as water, alcohols, acetic acid, alkyl halides, etc., whereby a proton or carbonium ion is generated by reaction of the halide and co-catalyst components.

The initiators which are usefully employed for initiating polymerization of the vinyl ether compounds and vinyl ether compositions of the present invention may also include onium salts, such as fluoride salts of aromatic diazonium compounds, and various polyboron salts. Preferred UV photocationic initiators are aryl onium salts, e.g., the 50% solution of triarylsulfonium salt in propylene carbonate solvent which is commercially available under the trademark Cyracure UVI-6974 from Union Carbide Corporation (Danbury, CT).

It will be recognized from the discussion of art in the Background of the Invention section hereof that there exist a wide variety of cationic photoinitiator constituents which may potentially be usefully employed in the broad practice of the present invention, with the choice of a specific photoinitiator for a given end use application being readily determinable by those skilled in the art without undue experimentation.

The aromatic vinyl ether compounds of the invention include those of the formula:

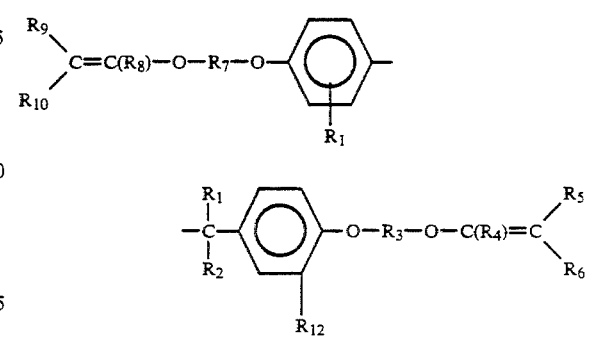

wherein:

$R_1$, $R_2$, $R_4$, $R_5$, $R_6$, $R_8$, $R_9$ and $R_{10}$ are independently selected from hydrogen, halogen, and $C_1$-$C_8$ alkyl radicals;

$R_3$ and $R_7$ are independently selected from $C_1$-$C_8$ alkylene radicals; and $R_{11}$ and $R_{12}$ are independently selected from allyl and methallyl.

Preferred aromatic vinyl ether compounds of the foregoing composition include those wherein $R_1$ and $R_2$ are independently selected from $C_1$-$C_4$ alkyl; $R_3$ and $R_7$ are $C_2$-$C_3$ alkylene; $R_4$, $R_5$, $R_6$, $R_8$, $R_9$, and $R_{10}$ are hydrogen; and $R_{11}$ and $R_{12}$ are allyl. Most preferably, $R_1$ and $R_2$ are methyl, $R_3$ and $R_7$ are ethylene, whereby the aromatic vinyl ether compound comprises a Bisphenol A residue in which the phenylene groups carry as ring carbon substituents allyl radicals, e.g., an aromatic vinyl ether compound of the formula:

readily cationically polymerizable in the presence of UV radiation and a suitable photoinitiator to form superior quality polymerized products, which are characterized by a very fast polymerization rate.

The foregoing diallyl Bisphenol A divinyl ether compound is characterized by a non-symmetric backbone structure as compared to the corresponding un-allylated Bisphenol A divinyl ether compound. As a consequence of this lack of backbone symmetry, the diallyl vinyl ether compound is a liquid at room temperature, while the corresponding un-allylated vinyl ether compound is a solid at room temperature.

More broadly, such approach of breaking or reducing the symmetry of an aromatic vinyl ether structure (to reduce the melting point of the vinyl ether compound relative to corresponding symmetric compounds) is embodied in the various monomers which are identified

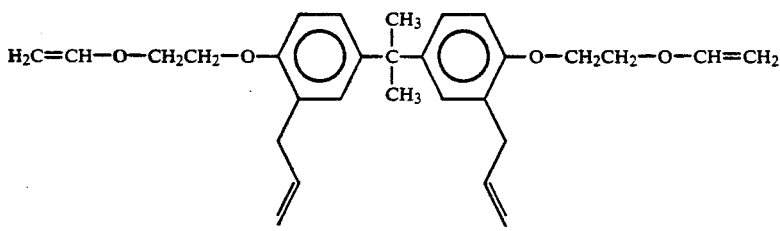

This compound, 2,2-bis(3-allyl, 4-vinyloxyethoxyphenyl) propane, is a free-flowing liquid monomer which is in Table I below, together with the melting point or physical state of these vinyl ether compounds.

TABLE I

| Vinyl Ether Compound | Melting point, °C. or Physical State |
|---|---|
| $H_2C=CH-O-CH_2CH_2-O-\text{[Bisphenol A diallyl divinyl ether structure]}$ | liquid |
| $CH_2=CH-O-CH_2-CH_2-O-\text{[t-Bu phenyl]}-O-CH_2-CH_2-O-CH=CH_2$ | liquid |
| $CH_2CH-O-CH_2-CH_2-O-\text{[phenyl]}-CO_2-CH_2-CH_2-O-CH=CH_2$ | 60 |
| $CH_2=CH-O-CH_2-CH_2-O-\text{[phenyl]}-CO_2-CH_2-CH_2-O-CH=CH_2$ | 44 |
| $CH_2=CH-O-CH_2-CH_2-O-\text{[phenyl]}-CO_2-CH_2-CH_2-O-CH=CH_2$ | 61-63 |

TABLE I-continued

| Vinyl Ether Compound | Melting point, °C. or Physical State |
|---|---|
| $CH_2=CH-O-CH_2-CH_2-O-\underset{Cl}{\underset{|}{\overset{Cl}{\overset{|}{C_6H_3}}}}-CO_2-CH_2-CH_2-O-CH=CH_2$ | liquid |
| $CH_2=CH-O-CH_2-CH_2-O-\underset{C_3H_7}{\underset{|}{\overset{C_3H_7}{\overset{|}{C_6H_3}}}}-CO_2-CH_2-CH_2-O-CH=CH_2$ | liquid |
| $CH_2=CH-O-CH_2-CH_2-O-(naphthyl)-CO_2-CH_2-CH_2-O-CH=CH_2$ | 41 |
| $CH_2=CH-O-CH_2-CH_2-O-(naphthyl)-CO_2-CH_2-CH_2-O-CH=CH_2$ | — |
| $CH_2=CH-O-CH_2-CH_2-O-C_6H_4-CH=CH-CO_2-CH_2-CH_2-O-CH=CH_2$ | liquid |
| $CH_2=CH-O-CH_2-CH_2-O-C_6H_3(CO_2-CH_2-CH_2-O-CH=CH_2)-O-CH_2-CH_2-O-CH=CH_2$ | 32–38 |
| $CH_2=CH-O-CH_2-CH_2-O-C_6H_3(O-CH_2-CH_2-O-CH=CH_2)-CO_2-CH_2-CH_2-O-CH=CH_2$ | |
| $CH_2=CH-O-CH_2-CH_2-O-C_6H_3(O-CH_2-CH_2-O-CH=CH_2)-CO_2-CH_2-CH_2-O-CH=CH_2$ | 49 |
| $CH_2=CH-O-CH_2-CH_2-O-C_6H_3(CO_2-CH_2-CH_2-O-CH=CH_2)-O-CH_2-CH_2-O-CH=CH_2$ | 41 |
| $CH_2=CH-O-CH_2-CH_2-O-C_6H_3(O-CH_2-CH_2-O-CH=CH_2)-CO_2-CH_2-CH_2-O-CH=CH_2$ | 56 |

TABLE I-continued

| Vinyl Ether Compound | Melting point, °C. or Physical State |
|---|---|
| H₂C=CH—O—CH₂CH₂—O—⟨C₆H₃(CH₃)⟩—C(CH₃)₂—⟨C₆H₃(CH₃)⟩—O—CH₂CH₂—O—CH=CH₂ | liquid |
| H₂C=C—O—CH₂—CH₂—O—⟨C₆H₃(CH₂CH₂CH₂CH₂CH₃)⟩—O—CH₂—CH₂—O—CH=CH₂ | liquid |

The vinyl ether compounds of the present invention may be formed in any suitable manner, as for example by reaction of aromatic polyols, such as aromatic diols, and corresponding carboxylic acids, or by reaction of the aromatic polyol with a suitable haloalkyl vinyl ether compound in the presence of base, such as is described in Crivello U.S. Pat. No. 4,705,887, or by corresponding reaction involving the use of a phase transfer catalyst, as described in Gallucci, R., et al, *J. Org. Chem.*, 48, 342-346 (1983).

For example, diallyl Bisphenol A divinyl ether may be made by reaction of diallyl Bisphenol A with chloroethyl vinyl ether in the presence of a base (hydroxide) in a suitable solvent, utilizing a quaternary ammonium halide phase transfer catalyst, as described hereinafter in greater detail.

The polyvinyl ether compounds of the present invention may be employed to form corresponding chain-extended monomers or oligomers, by reaction thereof with an active hydrogen compound, at a relative proportion of from about 0.1 to about 1 mole of active hydrogen compound per mole of the polyvinyl ether compound. The active hydrogen compound may be selected from carboxylic acids, aryl polyols, alkanols, thiols, and silanes, as described in U.S. Pat. No. 4,705,887. A preferred species of such chain-extension co-reactants are aryl polyols, most preferably bisphenolic compounds, e.g., Bisphenol A.

As an alternative approach to providing liquid aromatic vinyl ether compositions, the present invention also comprehends liquid vinyl ether blends comprising at least two vinyl ether compounds, at least one of which has a melting point above 25° C., and wherein the relative proportions of the respective vinyl ether compounds in the blend are such that the blend has a melting point below 25° C.

Although various vinyl ether compounds are known in the art, including compounds which are liquid at room temperature (e.g., the 5-t-butylcatechol divinyl ether compound disclosed at column 13, line 45 of U.S. Pat. No. 4,705,887), as well as vinyl ether compounds which are solid at room temperature (25° C.), it has not, to our knowledge, been recognized that solid vinyl ether compounds, or solid and liquid vinyl ether compounds, could be combined to form liquid vinyl ether blends having utility in applications such as coatings, sealants, and adhesives.

The present invention therefore contemplates liquid vinyl ether blends comprising vinyl ether compounds each of which has a melting point above 25° C., as well as liquid vinyl ether blends in which at least one vinyl ether compound has a melting point above 25° C. and at least one vinyl ether compound has a melting point below 25° C.

By way of illustration, and not limitation, the liquid vinyl ether blends in accordance with the present invention may comprise, subject to the restriction that at least one of the vinyl ether compounds has a melting point above 25° C., blends including vinyl ether compounds selected from those compounds identified in Table I hereof, and/or the additional aromatic vinyl ether compounds set out by way of example in Table II below.

TABLE II

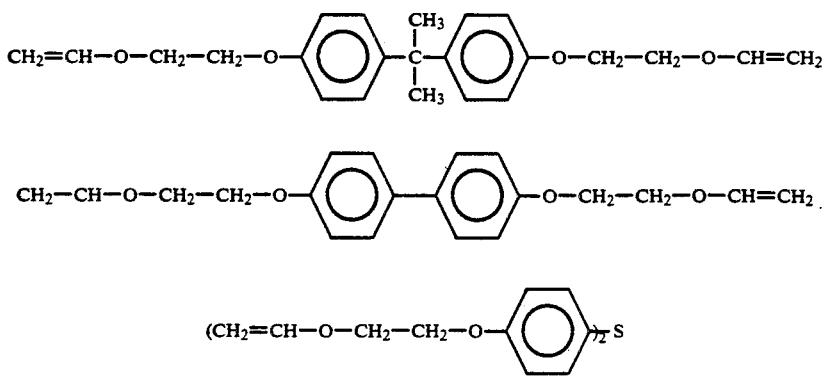

TABLE II-continued

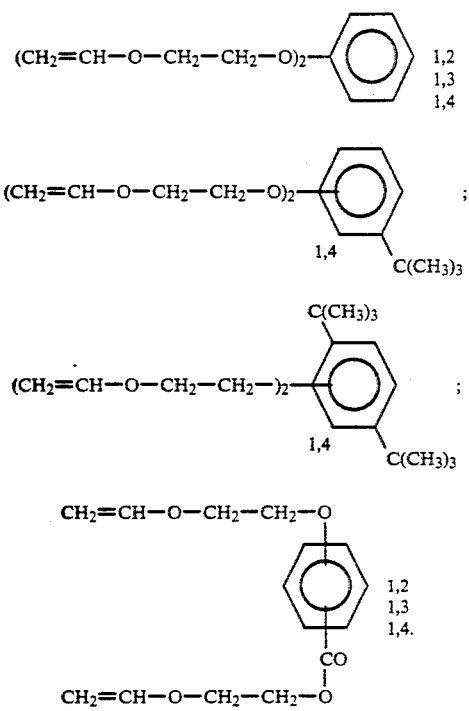

The specific proportions and vinyl ether compounds which may be employed to form such aromatic vinyl ether liquid blends from solid vinyl ether compounds, or combinations of liquid and solid vinyl ether compounds, are readily determinable by simple experiment, without undue effort. As used in this context, the terms "solid" and "liquid" refer to the physical state of the applicable vinyl ether compound(s) at 25° C. and standard pressure (1 atmosphere) conditions.

As an illustration of liquid vinyl ether blends of the present invention, a liquid blend may be formed by mixture of Bisphenol A divinyl ether, a solid at 25° C., and diallyl Bisphenol A divinyl ether, a liquid at 25° C., wherein the composition of the non-allylated vinyl ether compound to the allylated vinyl ether compound is in the range of from about 1:99 up to about 50:50 (at the upper limit of 50:50, elevated temperature mixing conditions initially produced a homogeneous liquid blend, but within 1 day at room temperature conditions, the 50:50 blend exhibited some recrystallization).

As a further illustration, salicyclic acid divinyl ether, a solid having a melting point of approximately 61°-63° C., may be mixed with the corresponding monovinyl ether in a suitable proportion, e.g., a 70:30 mixture of the divinyl compound to the monovinyl compounds, to provide a liquid vinyl ether blend at room temperature (25° C.).

The aromatic vinyl ether compounds, chain-extended derivatives, and/or liquid vinyl ether blends of the present invention may be employed as vinyl ether components of cationically curable vinyl ether compositions, when employed in combination with an effective amount of a cationic photoinitiator which is initiatingly effective for polymerization of the vinyl ether component in the presence of initiating radiation, such as UV radiation.

As previously discussed, the cationic photoinitiator may comprise any suitable initiator material which is effective to cationically polymerize the vinyl ether component in the curable composition when exposed to a suitable radiation source. Preferably, the cationic photoinitiator comprises an onium salt, more preferably an aryl onium salt, e.g., an aryl sulfonium salt. A particularly preferred photoinitiator is the triarylsulfonium salt (50% salt solution) in propylene carbonate solvent which is commercially available under the trademark Cyracure UVI-6974 from Union Carbide Corporation (Danbury, Conn.).

In general, the cationic photoinitiator may be employed at any suitable effective concentration, based on the amount of cationically polymerizable monomer present in the vinyl ether composition. In practice, when onium salts are employed as the photoinitiator constituent of the polymerizable composition, photoinitiator concentration levels on the order of from about 0.1% to about 5.0% by weight, based on the weight of the polymerizable vinyl ether material, and more preferably from about 0.2% to about 3% photoinitiator, on the same weight basis, may be usefully employed. Most preferably, from about 1% to about 2% by weight of photoinitiator is employed, when utilizing triarylsulfonium salts, to effect complete cure of the polymerizable material.

In a preferred method aspect, the present invention relates to a method of making an aromatic divinyl ether, in which a haloaliphatic vinyl ether compound is reacted with a polyhydroxy aromatic compound in the presence of base, e.g., sodium hydroxide, potassium hydroxide, etc., a quaternary ammonium halide phase transfer catalyst, and a solvent, to yield the aromatic divinyl ether as a reaction product.

The phase transfer catalyst may suitable comprise a tetraalkyl ammonium halide compound such as tetrabutyl ammonium bromide. Preferably, the tetralkyl ammonium halide compound comprises lower alkyl ($C_1$–$C_8$) substituents.

The solvent may comprise any suitable organic or inorganic solvent, including, for example, toluene, dimethylsulfoxide, chloroethyl vinyl ether, n-butyl alcohol, acetonitrile, etc. It has been found that aliphatic $C_7$–$C_{18}$ hydrocarbon solvents are unexpectedly superior in the achievement of high yields of the aromatic divinyl ether product, particularly when used with a stoichiometric excess (e.g., 100% or more) of the haloaliphatic vinyl ether reactant, so that the vinyl ether reactant functions as a co-solvent with the hydrocarbon solvent throughout the reaction. It has also been found that if dimethylsulfoxide is employed as the solvent, a phase transfer catalyst is not necessary to effectively carry out the reaction. A particularly preferred hydrocarbon solvent is heptane.

The haloaliphatic vinyl ether compound may for example comprise chloroethyl vinyl ether, and as mentioned, such compound may function both as a solvent in the reaction mixture, as well as a reactant therein. When chloroethyl vinyl ether is used as the solvent, it preferably is added at the beginning of the reaction, or if added subsequently is preferably of distilled purity.

The phase transfer catalyst preferably is introduced to the reaction at the inception thereof. The base in the reaction mixture preferably is potassium hydroxide or sodium hydroxide, and to ensure superior cure characteristics of the product aromatic divinyl ether, residual base in the recovered aromatic vinyl ether product preferably is substantially completely removed from the vinyl ether compound after the reaction is completed.

The temperature of the reaction mixture may be maintained or varied as suitable to obtain good production of the product aromatic divinyl ether. For example, reaction temperatures in the range of from about 80° C. to about 95° C. have been usefully employed, with the reaction beginning at the lower value of such range and being raised to the upper temperature thereof. It has also been found that a substantially uniform temperature of 90° C. is quite acceptable for carrying out the reaction. It should be noted, however, that if the reaction reaches reflux at the start, significant foaming is prone to result.

The concentration of catalyst employed in the reaction may be widely varied depending on the components of the reaction mixture and the reaction conditions employed. The specific catalyst concentration necessary or desirable for production of a specific aromatic divinyl ether product may be readily determined by those skilled in the art without undue experimentation. By way of example, catalyst concentrations on the order of from about 5 to about 10% are generally usefully employed when tetrabutyl ammonium bromide (TBAB) is employed as the catalyst, and are generally effective to complete the reaction within about 3 hours. The foregoing illustrative concentrations are by weight, based on the weight of the curable vinyl ether component in the composition.

The amount of base may likewise be widely varied, depending on the components and reaction conditions of the reaction mixture. It is generally desirable to provide a molar excess of base in the reaction mixture. In the case of sodium hydroxide or potassium hyroxide, it may be advantageous to employ the base at levels of from about 10 mole percent excess to about 25 mole percent excess.

It is highly desirable for all traces of base to be removed from the final product, because even small quantities of base can greatly inhibit cure. Traces of base can be neutralized in the product by addition of a suitable acid, followed by aqueous washing of the organic layer from the reaction product mixture. Alternatively, such organic layer may be washed with water, and thereafter treated with acidic alumina, followed by filtration; this acidic alumina treatment is preferred, to prevent any residual free acid from causing hydrolysis or slow polymerization of the vinyl ether product during storage thereof prior to its use.

Cationically polymerizable compositions according to the present invention, comprising aromatic vinyl ether compounds, chain-extended derivatives, and/or liquid vinyl ether blends as the vinyl ether component, in combination with an effective amount of a cationic photoinitiator, may be cured in exposure to suitable actinic radiation, such as UV radiation, to provide a polymeric material which is characterized by superior strength, toughness, rapid curing characteristics, and the other general advantages of cationically curable systems discussed earlier herein.

The aspects and features of the invention are more fully shown by the following non-limiting examples, wherein all parts and percentages are by weight, unless otherwise expressly stated.

EXAMPLE I

Bisphenol A divinyl ether, 2,2-(p-vinyloxyethoxyphenyl) propane, was synthesized by the method described in Crivello, J. V., and Conlon, D. A., *J. Polymer Sci., Polymer Chem. Ed.*, 21, 1785 (1983), using dimethylsulfoxide (DMSO) as a solvent, and with reaction of Bisphenol A with 2-chloroethylvinyl ether being carried out as in the published procedure. The Bisphenol A divinyl ether product was obtained at a yield of 70%, and had a melting point of 55° C.

EXAMPLE II

Diallyl Bisphenol A divinyl ether, 2,2-bis(3-allyl,4-vinyloxyethoxyphenyl) propane, was synthesized using the procedure described in Crivello, J. V., and Conlon, D. A., *J. Polymer Sci., Polymer Chem. Ed.*, 21, 1785 (1983), with dimethylsulfoxide (DMSO) as a solvent, and utilizing diallyl Bisphenol A (Matraimide 5292 System Part B, commercially available from Ciba-Geigy Company (Ardsley, N.Y.)) in place of Bisphenol A in the published procedure. The diallyl vinyl ether product was obtained at a 72% yield and 95% purity, as a liquid having a melting point below 25° C.

EXAMPLE III

Bisphenol A divinyl ether and diallyl Bisphenol A divinyl ether were prepared as described in Examples I and II, respectively. The resulting vinyl ether compounds then were blended with one another in the ratios set out in Table III below, and the physical state (liquid or solid) was identified after 24 hours, and after one week, with the blend being maintained at room temperature during and subsequent to initial mixture of the respective vinyl ether components. In the Table, Bisphenol A divinyl ether is denoted as "DVE-2" and the corresponding diallyl compound is denoted as "DVE-1."

TABLE III

| Blending Ratio | | State | |
|---|---|---|---|
| DVE-1 | DVE-2 | 24 Hr. | 1 Week |
| 100 | 0 | Liquid | Liquid |
| 75 | 25 | Liquid | Liquid |
| 50 | 50 | Liquid | Solid |
| 25 | 75 | Liquid | Solid |
| 0 | 100 | Solid | Solid |

As shown by the foregoing Table, the mixture of DVE-1:DVE-2 of from 100:0 to 25:75 remained in the liquid state at room temperature after 24 hours, and the 100:00 and 75:25 mixtures remained in the liquid state after one week. The 50:50 blend of DVE-1:DVE-2 remained liquid for at room temperature 24 hours after initial blending thereof; thereafter, partial solidification of the 50:50 blend was noted. The 25:75 blend at room temperature was totally solidified after one week.

EXAMPLE IV

A 500 ml four neck flask equipped with a condenser, mechanical stirrer, thermometer, and nitrogen inlet was charged with chlorethyl vinyl ether (100 ml), heptane (50 ml), Bisphenol A (45.6 g, 0.2 mole) and tetrabutyl ammonium bromide (4.6 g, 1.4 mmole). After stirring for 10 minutes at room temperature, sodium hydroxide (18 g, 0.45 moles) was added and the reaction mixture was heated to 90° C. After heating for 3 hours, the reaction was complete, as determined by HPLC.

Water (200 ml) was added to the reaction mixture, and the mixture was stirred until all of the solids dissolved. The reaction mixture then was placed into a separatory funnel and the aqueous layer removed. The organic layer was washed consecutively with 100 ml of saturated aqueous NaCl and 100 ml of water.

The organic layer then was dried (using $MgSO_4$ as a drying agent) and filtered. The filtrate was stirred with 10 g of acidic alumina for 10 minutes and filtered to remove any basic impurities. Solvent was removed under reduced pressure. The product was recrystallized from 100 ml of methanol. Yield=65.9 g (90%), M.P.=53°–55° C. The IR and NMR spectra confirmed the product as Bisphenol A divinyl ether.

EXAMPLE V

The procedure of Example IV was followed with t-butyl catechol (33.2 g, 0.2 mole) as the starting aromatic polyol material in place of Bisphenol A. The resulting product was a liquid, hence no recrystallization was required. Instead, the product was vacuum dried for 2 hours at 50° C. and 2.0 mm/Hg pressure after solvent was removed. Yield=55.9 g (92%). The IR and NMR spectra confirmed the product as t-butyl catechol divinyl ether.

EXAMPLE VI

The procedure of Example IV was utilized with diallyl Bisphenol A (DABPA) (61.6 g, 0.2 mole) as the starting material in place of Bisphenol A, using 6.44 g (20 mole) of tetrabutyl ammonium bromide as catalyst, and potassium hydroxide (28 g, 0.5 mole) as the base. Yield=81.5 g (91%). It is very important that DABPA is completely dissolved before addition of potassium hydroxide. The IR and NMR spectra confirmed the product as diallyl Bisphenol A divinyl ether.

EXAMPLE VII

To a four neck 250 ml round bottom flask equipped with a condenser, mechanical stirrer, thermometer, and nitrogen inlet was charged Bisphenol A divinyl ether made by the procedure of Example IV (95.8 g, 259 mmole), Bisphenol A (15 g, 65 mmole), and dichloroacetic acid (1.0 g, 7.7 mmole). The reaction mixture was heated to 100° C. and stirred until all of the hydroxyl absorption had disappeared in the IR spectrum (ca. 2 hrs.).

The reaction mixture then was dissolved in 200 ml of $CH_2Cl_2$ and washed once with 100 ml of saturated aqueous $NaHCO_3$ and three times with 100 ml of water. The organic layer was separated, dried (using $MgSO_4$ as the drying agent), and filtered. Solvent was removed under reduced pressure and the product was vacuum dried for one hour at 2.0 mm/Hg pressure and 50° C.; Yield=80 g (72%).

Infrared analysis confirmed that the reaction produced a chain-extended divinyl ether, in accordance with the following reaction scheme:

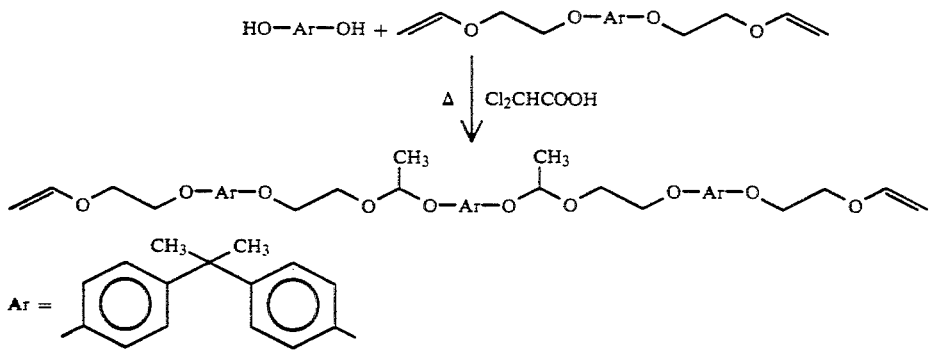

EXAMPLE VIII

The procedure of Example VII is repeated using diallyl Bisphenol A divinyl ether in place of Bisphenol A divinyl ether, and yield and purity levels of the corresponding allylated chain-extended vinyl ether product are comparable to those of the non-allylated product in Example VII.

EXAMPLE IX

Bisphenol A divinyl ether (DVE-3), t-butyl catechol divinyl ether (DVE-2), and diallyl Bisphenol A divinyl ether (DVE-1) were synthesized in accordance with the procedures of Examples IV, V, and VI, respectively.

The tensile strength, and flexural modulus of cured films of DVE-3, DVE-1, as well as DVE-3/DVE-2 and DVE-1/DVE-2 blends were determined.

Formulations were mixed to contain 1% by weight of photoinitiator, based on the weight of polymerizable material in the formulation, and 30 mil thick films were formed between glass plates treated with a Teflon® mold release compound, and containing a Teflon® spacer. Dogbone specimens were cut and pulled on an Instron tester at a cross-head speed of 2 inches per minute. An attempt was made to obtain samples of cured films of t-butyl catechol divinyl ether (DVE-2), but the resulting cured film was too brittle to obtain the necessary specimens. Flexural modulus was determined by the method of ASTM D-638.

The results of tensile strength and flexural modulus determination are set out in Table IV below.

TABLE IV

| Vinyl Ether Material | Tensile Strength (psi) | Flexural Modulus (psi) |
| --- | --- | --- |
| DVE-3 | 2620 | 132,000 |
| DVE-3/DVE-2 | 7585 | 321,000 |
| DVE-3/DVE-2 | 4359 | 235,000 |
| DVE-1 | 2620 | 132,000 |
| DVE-1/DVE-2 | 5455 | 306,000 |
| DVE-2/DVE-2 | 2945 | 242,000 |

EXAMPLE X

Bisphenol A divinyl ether (DVE-3) and diallyl Bisphenol A divinyl ether (DVE-1) were prepared according to the procedures of Examples IV and VI, respectively. Blends of DVE-3 and DVE-1 then were cured and the cured films were extracted with hexane.

In the extraction process, a known weight of the cured formulation was extracted for 18 hours in a Soxhlet Extractor. The pieces of sample then were removed, dried in a vacuum oven, and weighed. The weight difference then was determined, and the percent weight loss calculated.

The results of the solvent extraction tests on DVE-3/DVE-1 compositions of varying proportions are set out in Table V below.

TABLE V

| DVE-3/DVE-1 | % Extracted |
| --- | --- |
| 95/5 | 1/5 |
| 75/25 | 1.0 |
| 50/50 | 1.1 |
| 25/75 | 0.8 |
| 0/100 | 0 |

The average of approximately 1% extractable material in these samples corresponded to the amount of solvent present in the photoinitiator employed with the vinyl ether blend. It was therefore concluded that little or no vinyl ether resin remained unreacted in the cured films.

EXAMPLE XI

A 50/50 blend of DVE-3/DVE-1 was prepared as in Example X, and Shore D hardness was determined in accordance with the method of ASTM D-2240, for samples of the blend cured as in the procedure of Example IX.

Curing of the blend at 65 miliwatts per square centimeter of light intensity produced a cured film whose Shore D hardness decreased from approximately 80 immediately after curing to about 55 after two weeks. Corresponding cured samples in which the curing UV light intensity was reduced to 35 miliwatts per square centimeter yielded cured films having a Shore D hardness on the order of 75-80, which remained substantially constant for four weeks after curing.

EXAMPLE XII

A 50/50 blend of DVE-1/DVE-2 was made as in Example IX. Aliquots of the formulation were taken and respectively mixed with varying amounts of Cyracure UVI-6974 (Union Carbide Corporation, Danbury, Conn.), to yield vinyl ether compositions of 50/50 blends of DVE-1/DVE-2 containing 0.25, 0.5, 1.0, and 2.0 percent by weight of photoinitiator, based on the weight of the vinyl ether blend. Each side was cured as in the procedure of Example IX under 35 miliwatts per square centimeter of UV light intensity (20 seconds per side), and Shore D hardness measurements were taken on the cured film. A Shore D hardness of approximately 80 demonstrated that the film was completely cured. Results of this Shore D hardness determination are shown in Table VI below.

TABLE VI

| % Photoinitiator | Shore D Hardness |
| --- | --- |
| 0.25 | No Cure |
| 0.50 | Not Measureable |
| 1.00 | 77 |
| 2.00 | 78 |

Based on the foregoing, a minimum photoinitiator level on the order of about 1% by weight of the DVE-1/DVE-2 blend was required to effect substantially complete curing thereof.

EXAMPLE XIII

The chain-extended divinyl ether compound made by the procedure of Example VII was evaluated for sensitivity to atmospheric moisture (i.e., hydrolysis of the cured material). Cured films of the 4:1 DVE-3:Bisphenol A product obtained in Example VII exhibited an initial Shore D hardness value on the order of about 83, which however progressively (linearly) declined to a value of about 55 after 14 days ambient exposure.

While the invention has been described herein with reference to specific aspects, features, and embodiments, it will be appreciated that other variations, modifications, and embodiments therefore are possible, and all such variations, modifications, and embodiments therefor are to be regarded as being within the spirit and scope of the invention.

What is claimed is:

1. A cationically curable vinyl ether composition, comprising:

(a) a vinyl ether component selected from the group consisting of:

(i) aromatic vinyl ether components of the formula:

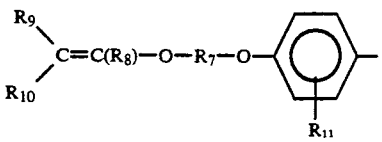

-continued

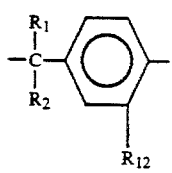

wherein:
R$_1$, R$_2$, R$_4$, R$_5$, R$_6$, R$_8$, R$_9$ and R$_{10}$ are independently selected from hydrogen, halogen, and C$_1$-C$_8$ alkyl radicals;
R$_3$ and R$_7$ are independently selected from C$_1$-C$_8$ alkylene radicals; and
R$_{11}$ and R$_{12}$ are independently selected from allyl and methallyl.
(ii) aryl polyol-reacted, chain-extended derivatives thereof; and (iii) mixtures of compounds (i) and/or (iii);
(b) an effective amount of a cationic photoinitiator which is initiatingly effective for polymerization of the vinyl ether component in the presence of initiating radiation.

2. A composition according to claim 1, wherein the vinyl ether component comprises a vinyl ether compound of the formula:

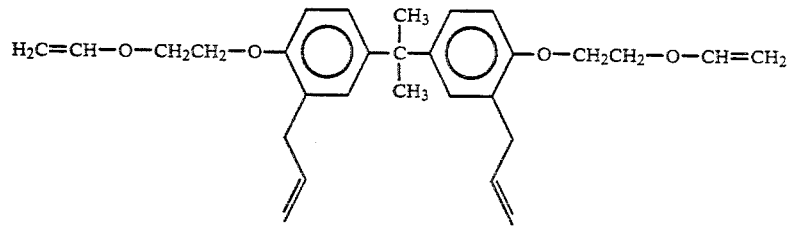

3. A composition according to claim 1, wherein the cationic photoinitiator comprises an onium salt.
4. A composition according to claim 1, wherein the cationic photoinitiator comprises an aryl sulfonium salt.
5. A composition according to claim 1, wherein the cationic photoinitiator comprises an aryl iodonium salt.
6. A cationically curable vinyl ether composition, comprising:
(a) a vinyl ether blend comprising at least two vinyl ether compounds, at least one of which has a melting point above 25° C., and wherein the relative proportions of the vinyl ether compounds in the blend are such the blend is a liquid at 25° C.; and
(b) an effective amount of a cationic photoinitiator which is initiatingly effective for polymerization of vinyl ether compounds in the blend, in the presence of initiating radiation.
7. A composition according to claim 6, wherein the blend comprises an aromatic vinyl ether compound.

* * * * *